United States Patent [19]

Woolard

[11] Patent Number: 4,874,873

[45] Date of Patent: Oct. 17, 1989

[54] PROCESS FOR THE PREPARATION OF 3-ACYLPYRROLIDONES

[75] Inventor: Frank X. Woolard, Richmond, Calif.

[73] Assignee: ICI Americas Inc., Wilmington, Del.

[21] Appl. No.: 290,219

[22] Filed: Dec. 27, 1988

[51] Int. Cl.[4] .................. C07D 207/46; A01N 43/36; A01N 43/40

[52] U.S. Cl. .................................. 548/540; 546/281

[58] Field of Search .................. 548/540; 546/281

[56] References Cited

PUBLICATIONS

CA 95(23:140709m—Abstract of Japanese Patent No. 46/24381, Jul. 13, 1971, Kobayashi et al.

CA 91(5):39819c—Abstract of: Synthesis of β-Carboxy-γ-Aminobutyric Acid; Danilova, E. M.; Derbeneva, V. P.; "Metody Sint. Str. Khim. Prevrashch, Nitrosedin, Gertsenovskie Chteniya", 31st, 27–30, (1978).

CA 54:12107f—Abstract of: Synthesis of γ-Amino Acids and Pyrrolidones; V. V. Perekalin et al., "Zhur. Obshchei Khim." 29, 2905–2910, (1959).

CA 31:9778f—Abstract of: Preparation of 2-Pyrrolidones and γ-Amino Acids, "Bull. Soc. Chim.", France, 1962, 598–603; Jean Cologne et al.

*Primary Examiner*—Mary C. Lee
*Assistant Examiner*—John A. H. Russell
*Attorney, Agent, or Firm*—Michael J. Bradley

[57] ABSTRACT

The process of the present invention provides 3-acylpyrrolidones by reaction of an anilino ketone with a diketene, followed by reduction with hydrogen in the presence of a noble metal catalyst. The products are useful as intermediates for pesticides.

12 Claims, No Drawings

PROCESS FOR THE PREPARATION OF 3-ACYLPYRROLIDONES

BACKGROUND OF THE INVENTION

The present invention is related to the preparation of 3-acylpyrrolidones.

The compounds to be synthesized, 3-acylpyrrolidones of the formula

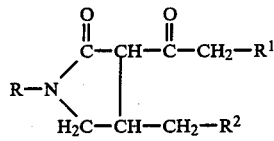

are useful as intermediates in the preparation of certain pesticides, and more particularly of certain herbicides.

Prior to the present invention, the primary method for synthesizing pyrrolidones used the reduction of a nitro group to an amine to form the 1,2-bond of the pyrrolidone ring. This method precludes the formation of a pyrrolidone ring in which the nitrogen atom is substituted with anything other than hydrogen. To substitue the nitrogen after the ring has been formed involves forcing conditions and the problem that the 3-position of the ring is more reactive.

A process has been described (Japanese publication JP 46/24381; CA 75(23):140709m) that allows for the introduction of a variety of substituents on the nitrogen, but it also results in mixtures of two different ring systems. In addition, to be useful as herbicide intermediates, the pyrrolidones that are formed must have the methylene group at the 3-position oxidized to a carboxylic acid and the carboxylic acid at the 4-position reduced to an alkyl group, a difficult and time-consuming procedure.

SUMMARY OF THE INVENTION

The process of the present invention provides 3-acylpyrrolidones by reaction of a ketone with a diketene, followed by reduction with hydrogen in the presence of a noble metal catalyst.

DETAILED DESCRIPTION OF THE INVENTION

More particularly, this invention is directed to a process for the manufacture of a compound having the formula

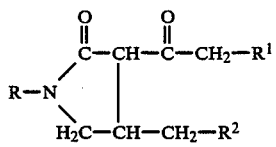

wherein,
R is lower alkyl, lower haloalkyl, lower cycloalkyl, lower cycloalkylalkyl, benzyl, chlorobenzyl or the group

in which each of X and Y is independently hydrogen, halogen, lower alkyl, lower haloalkyl, lower alkoxy, lower haloalkoxy, lower alkylsulfinyl, lower haloalkylsulfinyl, lower alkylsulfonyl, lower haloalkylsulfonyl, phenoxy, substituted phenoxy, pyridyloxy, or substituted pyridyloxy, $R^1$ is hydrogen or halogen; and
$R^2$ is hydrogen or lower alkyl;
which process comprises
(a) reacting a compound having the formula

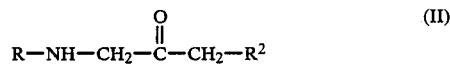

wherein R and $R^2$ are as defined above, with a diketene of the formula

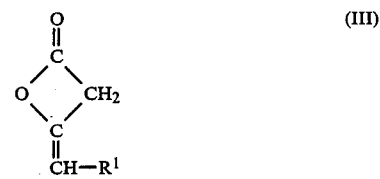

wherein $R^1$ is as defined above, in the presence of a catalytic amount of a tertiary amine, to give a pyrroliden-2-one of the formula

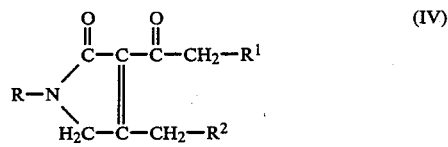

and,
(b) reducing the compound of formula IV with hydrogen gas in the presence of a noble metal catalyst to give a compound of formula I.

A noble metal catalyst may be chosen from those comprising gold, silver, platinum, iridium, rhodium, ruthenium or palladium chemically bound with other elements in the form of metal-containing compounds, such as salts and oxides. The metal-containing compounds can also be present in the form of complexes with common complexing agents, examples of which are triphenylphosphine and carbon monoxide. Advantageously, the noble metal catalysts are selected from those comprising platinum or palladium. Examples include palladium on carbon and platinum oxide. Platinum oxide is preferred. The noble metal catalysts may be used singly or in mixtures.

The noble metal catalyst is present in the reaction in a catalytic amount. The quantity which will constitute a "catalytic amount" will be any quantity that serves to increase the rate of reaction, with larger quantities providing a greater increase. The quantity used in any particular applicatin will be determined in large part by the individual needs of the manufacturing facility. Factors which enter into such a determination include the catalyst cost, recovery costs, desired reaction time, and system capacity. Aside from these considerations, the catalyst quantity is not a critical feature of the invention and can vary over a wide range. It will be most convenient to use an amount of catalyst which comprises from about 0.01 to about 20.0 mole percent, preferably from about 0.1 to about 10.0 mole percent based on the pyrroliden-2-one of formula IV.

Examples of a tertiary amine which may be used in the present invention include triethylamine, diazabicyclooctane (DABCO) and 4,4-dimethylaminopyridine (DMAP). DMAP is preferred. The tertiary amines may be used singly or as mixtures. A "catalytic amount" is as defined hereinabove and comprises from about 0.01 to about 20.0 mole percent, preferably from about 0.1 to about 10.0 mole percent of the tertiary amine, based on the ketone of formula II.

The process may successfully be run over a wide range of temperatures. The operating temperature may range from about 10° C. to the reflux temperature of the solvent used. However, temperature control is often desirable since, for example, the reaction a) will run more quickly at higher temperatures. The preferable temperature range of reaction (a), therefore, is from about 20° C. to the reflux temperature of the solvent. The preferable temperature range of reaction (b) is from about 15° C. to about 40° C.

The process does not have a critical operating pressure, but is operable over a wide pressure range, subject only to considerations of time, economy, process convenience and materials of construction. It is most convenient, however, to conduct the reaction (a) at approximately atmospheric pressure. It is most convenient to conduct the reaction (b) at a pressure of from about 0 to about 60 psig, preferably from about 5 to about 60 psig and more preferably of about 35-55 psig.

For maximum efficiency, the reaction is preferably run using an excess of the diketene of formula III. While the amount of excess is purely a question of process economy, such as raw material costs and recovery expenses, the reaction is most conveniently run at a diketene excess of up to about 35%.

A variety of solvents can be used in the practice of the present invention. Any inert solvent can be used, including, but not limited to the following: aliphatic compounds, for example hexane or octane; aromatic compounds, for example benzene, toluene, xylene or mesitylene; chlorinated aliphatic or aromatic compounds, for example methylene chloride, ethylene dichloride or chlorobenzene; ethers, for example 1,2-dimethoxyethane, diethyl ether, tetrahydrofuran or 1,4-dioxane; alcohols, for example isopropanol or ethylene glycol; ketones, for example acetone, methyl ethyl ketone or methyl isobutyl ketone; amides, for example N,N-dimethylformamide or N-methylpyrrolidinone; nitriles, for example acetonitrile or butyronitrile; and carboxylic acids and their esters, for example acetic, propionic or butyric acid or ethyl acetate.

The 3-acylpyrrolidones produced by the reaction of the invention can be recovered from the reaction mixture by any conventional technique.

As used in this specification and the attached claims:

The term "lower alkyl" refers to an alkyl group, straight or branched, of one to six carbon atoms.

The term "lower cycloalkyl" refers to a cycloalkyl group of three to seven carbon atoms.

The term "lower cycloalkylalkyl" refers to a lower cycloalkyl group substituted at one of the ring carbons with a lower alkyl group, the total number of carbon atoms being from four to eight.

The term "lower alkoxy" refers to an alkoxy group, straight or branched, of one to six carbon atoms.

The term "lower alkylsulfinyl" refers to an alkylsulfinyl group, straight or branched, of one to six carbon atoms.

The term "lower alkylsulfonyl" refers to an alkylsulfonyl group, straight or branched, of one to six carbon atoms.

The terms "lower haloalkyl", "lower haloalkoxy", "lower haloalkylsulfinyl" and "lower haloalkylsulfonyl" refer to a lower alkyl group, a lower alkoxy group, a lower alkylsulfinyl group, and a lower alkylsulfonyl group, respectively, substituted by one or more halogen atoms. Such halogen is preferably fluoro.

The terms "substituted phenoxy" and "substituted pyridyloxy" refer to a phenoxy group and a pyridyloxy group, respectively, substituted at one to five of the carbon atoms with groups such as halogen, lower alkyl, lower haloalkyl, lower alkoxy or lower haloalkoxy.

Where any of the substituents R, $R^1$, X and Y is or comprises halogen, such halogen is conveniently selected from bromo, chloro or fluoro.

Within the scope of the above description, certain embodiments are preferred.

In R, the phenyl group substituted with X and Y is preferred.

Conveniently, X and Y are selected from hydrogen, halogen, $C_{1-4}$ alkyl, trifluoromethyl, trifluoromethylsulfinyl, and trifluoromethylsulfonyl. In X, bromo, chloro, $C_{1-4}$ alkyl, and trifluoromethyl are preferred, and trifluoromethyl is more preferred. In Y, hydrogen and $C_{1-4}$ alkyl are preferred, and hydrogen is more preferred.

In $R^1$, hydrogen is preferred.

In $R^2$, hydrogen and $C_{1-4}$ alkyl are preferred, and methyl is more preferred.

The starting ketone of formula II is prepared by the reaction of the corresponding alcohol (V) with a reagent that will form a carbamate. This can be accomplished with a variety of alkyl chloroformates or anhydrides and is preferably conducted with di-t-butyldicarbonate. The reaction can be conducted without solvent, at between 80° C. and 100° C. The resulting carbamate is then oxidized to the ketone under basic to neutral conditions using either aqueous sodium hypochlorite or pyridine dichromate in refluxing methylene chloride. The ketone is treated with anhydrous HCl gas to give the hydrochloride of the ketone (II).

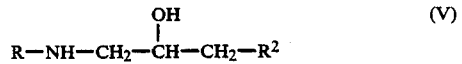

$$R-NH-CH_2-\overset{\overset{OH}{|}}{CH}-CH_2-R^2 \qquad (V)$$

Alcohols of formula V are known (see, e.g. U.S. Pat. No. 4,723,986) or, in those cases where they may not be known, they may be synthesized by processes known in the art.

The starting diketene of formula III is known or, if it is not known, it may be synthesized by processes known in the art.

The process of the present invention is further illustrated by the following examples. These examples are offered strictly for purposes of illustration, and are not intended to either limit or to define the invention.

EXAMPLE 1

This example illustrates the preparation of N-(2-oxo)-butyl-3-aminobenzotrifluoride hydrochloride.

A mixture of N-(2-hydroxy)butyl-3-aminobenzotrifluoride (106.86 g, 0.458 mol) and di-t-butyl dicarbonate (110.0 g, 0.504 mol), under $N_2$, was heated on a steam bath with occasional swirling. After 10 hours, gas evolution had ceased. The crude product was then combined with ether (300 mL), washed with water (3×250 mL) and with saturated NaCl solution (1×250 mL), and dried over $Na_2SO_4$, after which the solvent was removed to give N-(2-hydroxy)butyl-N-t-butoxy-carbonyl-3-aminobenzotrifluoride (152.73 g, 100%) as a thick colorless oil.

A suspension of pyridinium dichromate (86.14 g, 0.229 mol), methylene chloride (200 mL), trifluoroacetic acid (7.70 g, 4.53 mL) and pyridine (4.75 g, 4.86 mL, 0.060 mol) was stirred and heated to a gentle reflux. N-(2-hydroxy)-butyl-N-t-butoxycarbonyl-3-aminobenzotrifluoride (51.0 g, 0.153 mol) in 100 mL of methylene chloride was added dropwise over one hour. When the addition was complete, the refluxing was continued for another 8 hours. The heating was then discontinued and the stirring was continued overnight at room temperature. The suspension was then diluted with 400 mL of ether to precipitate the inorganic salts and was filtered through diatomaceous earth. Removal of the solvents under reduced pressure provided a dark oil that was flash chromatographed on silica gel with ether as eluent. The resulting tan oil was taken up in 400 mL of ether and rapidly stirred, and the solution was saturated at room temperature with anhydrous HCl gas. After stirring overnight, the precipitated product was isolated by vacuum filtration to yield 30.61 g (75%) of N-(2-oxy)butyl-3-aminobenzotrifluoride hydrochloride as a white powder, m.p. 113° C. dec., the structure of which was confirmed by NMR, IR and MS.

EXAMPLE 2

This example illustrates the preparation of 1-(3-trifluoromethyl)phenyl-3-acetyl-4-ethyl-$\Delta^{3,4}$-pyrroliden-2-one.

A solution of N-(2-oxo)butyl-3-aminobenzotrifluoride (9.41 g, 40.7 mmol) in acetone (20 mL) and DMAP (20 mg) was stirred and heat to refluxing, and a solution of 50% diketene in acetone (16.16 mL, 13.69 g, 81.4 mmol) was added dropwise over 5 min. When the addition was complete, the refluxing was continued for an additional 15 min. and the solvent was then removed under reduced pressure to give 12.10 g (100%) of 1-(3-trifluoromethyl)phenyl-3 -acetyl-4-ethyl-$\Delta^{3,4}$-pyrroliden-2-one, a red oil, the structure of which was confirmed by NMR, IR, and MS.

EXAMPLE 3

This example illustrates the synthesis of 1-(3-trifluoromethyl)phenyl-3-acetyl-4-ethyl-2-pyrrolidone.

A solution of 1-(3-trifluoromethyl)phenyl-3-acetyl-4-ethyl-$\Delta^{3,4}$-pyrroliden-2-one (3.32 g, 11.2 mmol) in 25 mL of ethyl acetate was placed in a hydrogenation bottle with 20 mg of platinum oxide. The bottle was then placed on a Paar apparatus and the reduction was initiated at a hydrogen pressure of 50 psig. After 1 hr., when hydrogen uptake had ceased, the catalyst was removed by filtration through a pad of diatomaceous earth and the solvent was removed under reduced pressure to give 3.34 g (100%) of 1-(3-trifluoromethyl)phenyl-3-acetyl-4-ethyl-2-pyrrolidone as a red oil, the structure of which was confirmed by NMR, IR and MS.

Although the present invention has been described in some detail by way of example for purposes of clarity and understanding, it will be apparent that other arrangements and equivalents are possible and may be employed without departing from the spirit and scope of the invention. Therefore, the description and illustrations should not be construed as limiting the scope of the invention, which is delineated by the appended claims.

What is claimed is:

1. A process for the manufacture of a compound having the formula

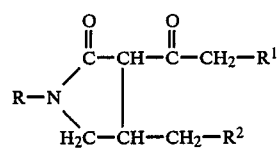

wherein

R is lower alkyl, lower haloalkyl, lower cycloalkyl, lower cycloalkylalkyl, benzyl, chlorobenzyl or the group

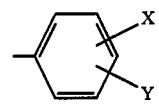

in which each of X and Y is independently hydrogen, halogen, lower alkyl, lower haloalkyl, lower alkoxy, lower haloalkoxy, lower alkylsulfinyl, lower haloalkylsulfinyl, lower alkylsulfonyl, lower haloalkylsulfonyl, phenoxy, substituted phenoxy, pyridyloxy, or substituted pyridyloxy;

$R^1$ is hydrogen or halogen; and $R^2$ is hydrogen or lower alkyl; which process comprises (a) reacting a compound having the formula

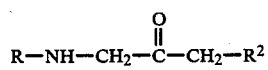

wherein R and $R^2$ are as defined above, with a diketene of the formula

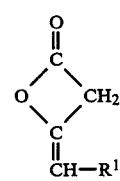

wherein $R^1$ is as defined above, in the presence of a catalytic amount of a tertiary amine, to give a pyrroliden-2-one of the formula

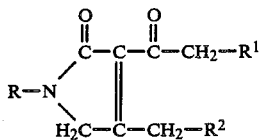

and, (b) reducing the compound of formula IV with hydrogen gas in the presence of a noble metal catalyst to give a compound of formula I.

2. A process according to claim 1 wherein said noble metal catalyst comprises platinum or palladium.

3. A process according to claim 2 wherein said noble metal catalyst is platinum oxide or palladium on carbon.

4. A process according to claim 1 wherein said noble metal catalyst is present in an amount of from about 0.01 to about 20.0 mole percent.

5. A process according to claim 1 wherein said noble metal catalyst is present in an amount of from about 0.1 to about 10.0 mole percent.

6. A process according to claim 1 wherein said tertiary amine is selected from triethylamine, diazabicyclooctane and 4,4-dimethylaminopyridine.

7. A process according to claim 1 wherein said tertiary amine is present in an amount of from about 0.01 to about 20.0 mole percent.

8. A process according to claim 1 wherein said tertiary amine is present in an amount of from about 0.1 to about 10.0 mole percent.

9. A process according to claim 1 wherein reaction (a) takes place at a temperature of from about 10° C. to the reflux temperature of the solvent used, and reaction (b) takes place at a temperature of from about 15° C. to about 40° C.

10. A process according to claim 1 wherein R is the group

$R^1$ is hydrogen and $R^2$ is hydrogen or lower alkyl of 1 to 4 carbon atoms.

11. A process according to claim 10 wherein each of X and Y is independently hydrogen, bromo, chloro, lower alkyl of 1 to 4 carbon atoms, trifluoromethyl, trifluoromethylsulfinyl or trifluoromethylsulfonyl.

12. A process according to claim 11 wherein X is trifluoromethyl and Y is hydrogen.

* * * * *